United States Patent
Ohara

(10) Patent No.: US 12,249,088 B2
(45) Date of Patent: Mar. 11, 2025

(54) CONTROL DEVICE, IMAGE PROCESSING METHOD, AND STORAGE MEDIUM

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 453 days.

(21) Appl. No.: 17/684,557

(22) Filed: Mar. 2, 2022

(65) Prior Publication Data

US 2022/0222840 A1 Jul. 14, 2022

Related U.S. Application Data

(63) Continuation of application No. PCT/JP2019/035012, filed on Sep. 5, 2019.

(51) Int. Cl.
*G06T 7/55* (2017.01)
*A61B 1/00* (2006.01)
*G06T 7/70* (2017.01)

(52) U.S. Cl.
CPC .......... *G06T 7/55* (2017.01); *A61B 1/000095* (2022.02); *A61B 1/000096* (2022.02);
(Continued)

(58) Field of Classification Search
CPC ... G06T 7/55; G06T 7/70; G06T 2207/10024; G06T 2207/10048; G06T 2207/10064; G06T 2207/10068; G06T 2207/10152; G06T 2207/20081; G06T 2207/30004; G06T 2207/30244; G06T 2207/20084; G06T 2207/30101; A61B 1/000095;
(Continued)

(56) References Cited

U.S. PATENT DOCUMENTS 6,063,023 A 5/2000 Sakiyama et al.
2009/0147999 A1 6/2009 Maeda et al.
(Continued)

FOREIGN PATENT DOCUMENTS

CN 109934831 A 6/2019
JP H10-248806 A 9/1998
(Continued)

OTHER PUBLICATIONS

International Search Report dated Nov. 12, 2019 issued in PCT/JP2019/035012.
(Continued)

*Primary Examiner* — Dhaval V Patel
(74) *Attorney, Agent, or Firm* — Scully, Scott, Murphy & Presser, P.C.

(57) ABSTRACT

A control device includes a processor including hardware. The processor acquires a surface image of a surface of an observation target and an inside image of a target portion existing inside the observation target, calculates three-dimensional coordinates of the surface from the surface image, calculates three-dimensional coordinates of the target portion from the inside image, and estimates depth information indicating a depth from the surface to the target portion based on the three-dimensional coordinates of the surface and the three-dimensional coordinates of the target portion.

20 Claims, 11 Drawing Sheets

(52) U.S. Cl.
CPC ...... *G06T 7/70* (2017.01); *G06T 2207/10024* (2013.01); *G06T 2207/10048* (2013.01); *G06T 2207/10064* (2013.01); *G06T 2207/10068* (2013.01); *G06T 2207/10152* (2013.01); *G06T 2207/20081* (2013.01); *G06T 2207/30004* (2013.01); *G06T 2207/30244* (2013.01)

(58) Field of Classification Search
CPC .......... A61B 1/000096; A61B 1/00096; A61B 1/00186; A61B 1/046; A61B 1/05; A61B 1/0655; A61B 1/0638; A61B 1/045; A61B 1/0669; A61B 1/07
See application file for complete search history.

(56) References Cited

U.S. PATENT DOCUMENTS

| | | | |
|---|---|---|---|
| 2015/0049167 A1* | 2/2015 | Suzuki | A61B 1/0057 348/45 |
| 2017/0007350 A1* | 1/2017 | Popovic | A61B 1/00009 |
| 2017/0209031 A1* | 7/2017 | Nakamura | A61B 1/000094 |
| 2018/0192982 A1 | 7/2018 | Pereira et al. | |
| 2019/0021579 A1 | 1/2019 | Kamon | |
| 2019/0038111 A1 | 2/2019 | Endo | |
| 2019/0065905 A1 | 2/2019 | Rephaeli et al. | |
| 2020/0297422 A1 | 9/2020 | Gocho et al. | |
| 2021/0169305 A1 | 6/2021 | Fukazawa et al. | |

FOREIGN PATENT DOCUMENTS

| | | |
|---|---|---|
| JP | 2009-160386 A | 7/2009 |
| JP | 2016-093210 A | 5/2016 |
| JP | 2017-184861 A | 10/2017 |
| JP | 2017-192565 A | 10/2017 |
| JP | 2017-192594 A | 10/2017 |
| WO | 2016/013636 A1 | 1/2016 |
| WO | 2018/128957 A1 | 7/2018 |
| WO | 2019/092950 A1 | 5/2019 |
| WO | 2019/116592 A1 | 6/2019 |

OTHER PUBLICATIONS

Japanese Office Action dated Dec. 13, 2022 received in 2021-543899.

Japanese Office Action dated Oct. 24, 2023 received in 2021-543899.

Japanese Office Action dated May 30, 2023 received in 2021-543899.

* cited by examiner

CONTROL DEVICE, IMAGE PROCESSING METHOD, AND STORAGE MEDIUM

CROSS REFERENCE TO RELATED APPLICATION

This application is a continuation of International Patent Application No. PCT/JP2019/035012, having an international filing date of Sep. 5, 2019, which designated the United States, the entirety of which is incorporated herein by reference.

BACKGROUND

There are known methods for performing observation using special light as well as observation using white illumination light in diagnosis and treatment using medical endoscopes. The observation using the special light includes observation using fluorescence caused by a reagent such as fluorescence observation using ICG (indocyanine green), and observation using a plurality of types of illumination light having different wavelengths such as NBI (narrow band imaging). In such special light observation, a depth of a target portion in a living body part is important information for improving diagnosis accuracy and determining a treatment course.

For example, Japanese Unexamined Patent Application Publication No. 2017-192594 discloses a method for estimating a depth of a blood vessel based on brightness or contrast of the blood vessel and switching the illumination light to the one suitable for the observation of the blood vessel in question.

SUMMARY

In accordance with one of some aspect, there is provided a control device comprising a processor including hardware, the processor being configured to:
acquire a surface image of a surface of an observation target and an inside image of a target portion existing inside the observation target;
calculate three-dimensional coordinates of the surface based on the surface image;
calculate three-dimensional coordinates of the target portion based on the inside image; and
estimate depth information indicating a depth from the surface to the target portion based on the three-dimensional coordinates of the surface and the three-dimensional coordinates of the target portion.

In accordance with one of some aspect, there is provided an image processing method comprising:
acquiring a surface image of a surface of an observation target and an inside image of a target portion existing inside the observation target;
calculating three-dimensional coordinates of the surface from the surface image;
calculating three-dimensional coordinates of the target portion from the inside image; and
estimating depth information indicating a depth from the surface to the target portion based on the three-dimensional coordinates of the surface and the three-dimensional coordinates of the target portion.

In accordance with one of some aspect, there is provided a computer-readable non-transitory storage medium configured to store a program that causes a computer to perform steps of:
acquiring a surface image of a surface of an observation target and an inside image of a target portion existing inside the observation target;
calculating three-dimensional coordinates of the surface from the surface image;
calculating three-dimensional coordinates of the target portion from the inside image; and
estimating depth information indicating a depth from the surface to the target portion based on the three-dimensional coordinates of the surface and the three-dimensional coordinates of the target portion.

DESCRIPTION OF EXEMPLARY EMBODIMENTS

Figure 1:
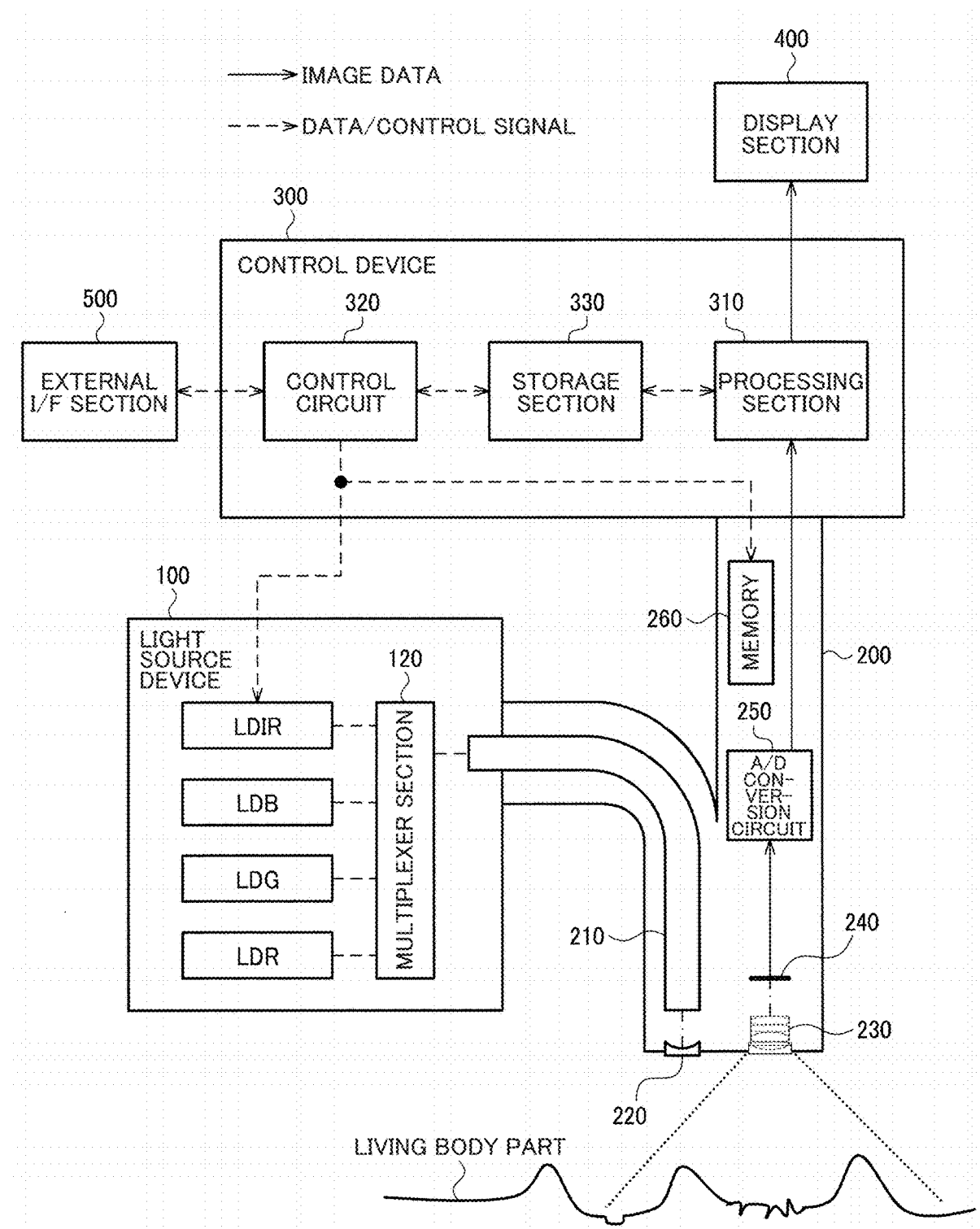
FIG. 1 is a configuration example of an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. Endoscope System

FIG. 1 is a configuration example of an endoscope system. The endoscope system includes an insertion section 200, a control device 300, a display section 400, an external I/F section 500, and a light source device 100. The endoscope system may include a rigid scope used for a laparoscope or the like, for example. However, the endoscope system is not limited to the rigid scope, and may be a flexible scope used for a digestive tract or the like, or any other device. The insertion section 200 is also referred to as a scope. The scope may include part of the external I/F section 500 in addition to the insertion section 200, and the scope is connected to the control device 300 via a connecting cable unillustrated. The control device 300 is also referred to as a main body section or a processing device. The display section 400 is also referred to as a display device. The external I/F section 500 is also referred to as an operation section or an operation device. The light source device 100 is also referred to as an illumination section or an illumination device.

The light source device 100 is a device emitting illumination light. The light source device 100 includes light sources LDB, LDG, LDR, and LDIR, and a multiplexer section 120. Each of the light sources LDB, LDG, LDR, and LDIR is an LED (light emitting diode) or a laser light source. The light emitted by the light sources LDB, LDG, LDR, and LDIR are hereinafter referred to as B light, G light, R light, and IR light, respectively.

The B light is light in a blue wavelength band included in white light. The G light is light in a green wavelength band included in the white light. The R light is light in a red wavelength band included in the white light. For example, the wavelength band of the B light is from 430 to 500 nm, the wavelength band of the G light is from 500 to 600 nm, and the wavelength band of the R light is from 600 to 700 nm. The IR light is infrared light having a peak wavelength of 780 nm. The IR light is used for fluorescence observation. For example, a fluorescent pigment of ICG (indocyanine green) absorbs the infrared light around 780 nm and emits fluorescence around 805 nm. The ICG is used as an agent for the fluorescence observation, and is applied by splaying in a living body, intravenous injection, or the like.

The wavelengths described above are only examples. For example, the peak wavelength, or upper and lower limits of the wavelength band of each light may vary by 10% or so. The B light, G light, and R light may be narrow band light having a half-value width of several to several tens nm. The light source device 100 may include a light source unillustrated that emits light in another wavelength band. For example, the light source device 100 may include a light source that emits V light of narrow band light in the blue wavelength band. The V light is the narrow band light having the peak wavelength in a range from 390 to 445 nm. A modified embodiment including the V light will be described later.

The multiplexer section 120 multiplexes the light emitted by the light sources LDB, LDG, LDR, and LDIR, and inputs the multiplexed light into a light guide 210. The multiplexer section 120 includes a dichroic mirror, a lens, or the like, for example.

The light source device 100 emits one or some of the B light, G light, R light, and IR light of one or some wavelengths at a single emission timing. The single emission timing used here means a timing corresponding to single-time imaging by an image sensor 240, that is, one frame of imaging. Accordingly, the endoscope system according to the present embodiment acquires an image captured in one frame based on the light emitted from the light source device 100 at the single emission timing. As will be described later, light emission by the light sources is not limited to continuous light emission, and may be pulse light emission. The single emission timing in the latter case includes a plurality of times of pulse light emission in a time period corresponding to one frame. The light of one or some wavelengths emitted at the single emission timing is hereinafter referred to as an illumination light group. Details of illumination will be described later.

The insertion section 200 is inserted into a living body. The insertion section 200 includes a light guide 210, an illumination lens 220, an objective lens 230, an image sensor 240, and an A/D conversion circuit 250. The insertion section 200 can also include a memory 260. The image sensor 240 is also referred to as an image sensor. The insertion section 200 includes a connector unillustrated, and is attached to or detached from the control device 300 via the connector. As described above, the insertion section 200 may be connected with the control device 300 via the connecting cable.

The light guide 210 guides the illumination light emitted from the light source device 100 to a distal end of the insertion section 200. The illumination lens 220 applies the illumination light guided by the light guide 210 to an object. The object in the present embodiment is a living body part. Reflected light from the object enters the objective lens 230. The objective lens 230 forms an object image, and the image sensor 240 captures the object image.

The image sensor 240 includes a plurality of pixels that photoelectrically convert the object image, and acquires pixel signals from the plurality of pixels. The image sensor 240 is a color image sensor capable of acquiring the pixel signals of a plurality of colors per single-time imaging, for example. The image sensor 240 includes a color filter array including a blue color filter sensitive to the blue wavelength band, a green color filter sensitive to the green wavelength band, and a red color filter sensitive to the red wavelength band, for example. The blue, green, and red color filters are hereinafter referred to as a B filter, a G filter, and an R filter, respectively. The image sensor 240 may be a sensor including a color filter array of a widely known Bayer array. However, the configuration of the image sensor 240 is not limited to this, and the image sensor may be a sensor including a color filter array where the R filter, G filter, and B filter are arranged differently, or a sensor including a color filter array including complementary color filters. The complementary color filters include color filters of cyan, magenta, and yellow, for example.

The A/D conversion circuit 250 converts analog pixel signals output from the image sensor 240 into digital pixel signals. The A/D conversion circuit 250 may be embedded in the image sensor 240.

The control device 300 performs signal processing including image processing. The control device 300 also controls sections in the endoscope system. The control device 300 includes a processing section 310, a control circuit 320, and a storage section 330. The control circuit 320 controls the sections in the endoscope system. For example, a user operates the external I/F section 500 and sets a display mode. For example, when a selection of a display mode for displaying depth information as three-dimensional shape information, described later, is input, the control circuit 320 outputs an instruction to the processing section 310 to perform a generation process of a display image including the depth information. The processing section 310 performs an estimation process of the three-dimensional shape information and the generation process of the display image in response to the instruction from the control circuit 320. The storage section 330 functions as a work area for the processing section 310 or the like, and this function can be implemented with a memory such as a RAM (random access memory) and an HDD (hard disk drive). The storage section 330 may store a trained model, as will be described later.

The memory 260 in the insertion section 200 stores information on the insertion section 200. The control circuit 320 controls the sections of the endoscope system based on the information read out from the memory 260. For example, the memory 260 stores information on the image sensor 240. The information on the image sensor 240 includes a type of the image sensor 240, for example. The control circuit 320 causes the processing section 310 to perform the image processing suitable for and based on the information on the image sensor 240 read out from the memory 260.

The processing section 310 performs the image processing based on the pixel signals from the A/D conversion circuit 250 to generate the display image and output the display image to the display section 400. The display section 400 is a liquid crystal display device, for example, and displays the display image received from the processing section 310. As will be described later, the display section 400 may be a display device capable of displaying a three-dimensional image.

Figure 2:
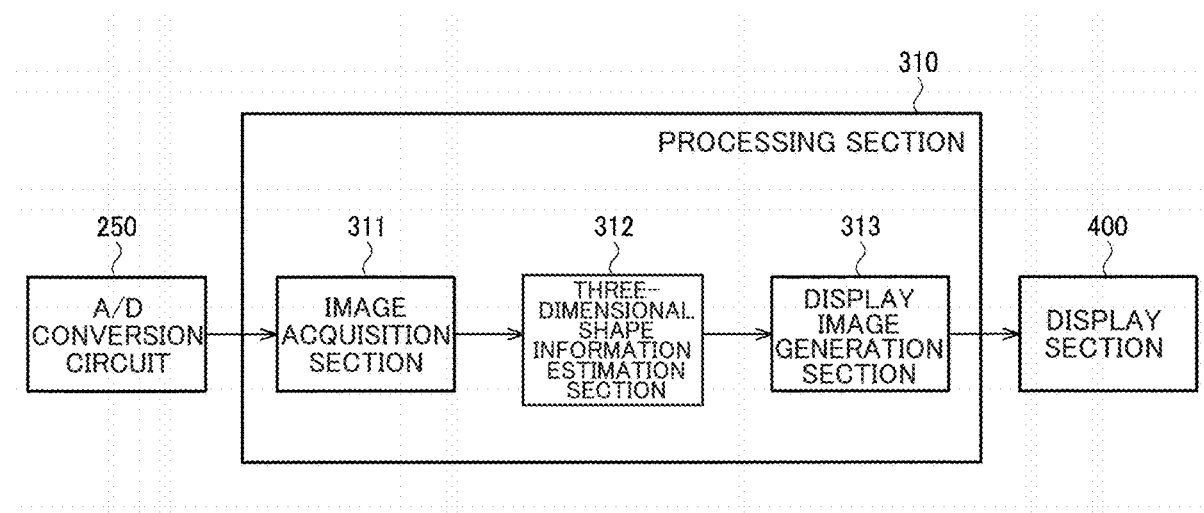
FIG. 2 is a detailed configuration example of a processing section.

FIG. 2 is a detailed configuration example of the processing section 310. The processing section 310 includes an image acquisition section 311, a three-dimensional shape information estimation section 312, and a display image generation section 313.

The image acquisition section 311 receives the input of the pixel signals from the A/D conversion circuit 250. The image acquisition section 311 acquires a B image, a G image, an R image, and an IR image based on the pixel signals. The B image is an image acquired by a B pixel, the G image is an image acquired by a G pixel, and the R image is an image acquired by an R pixel when the white light including the B light, G light, and R light is emitted. The IR image is an image acquired by a pixel sensitive to the IR right when the IR light is emitted. The B pixel is a pixel that receives the light transmitted by the B filter described above. Similarly, the G pixel is a pixel that receives the light transmitted by the G filter, and the R pixel is a pixel that receives the light transmitted by the R filter.

The image acquisition section 311 inputs the R image, G image, and B image to an R channel, a G channel, and a B channel of a color image, respectively, so as to generate a white light image. The white light image includes components in the wavelength band corresponding to visible light. Thus, the white light image includes both surface information and inside information of an observation target that is the living body part. The white light image largely includes components relating to the surface of the observation target, and thus the white light image is an image mainly showing a surface shape of the observation target. On the other hand, the IR image includes a fluorescent component due to the ICG as described above. The ICG has a property to accumulate in a specific part such as a tumor. Accordingly, the IR image mostly includes components relating to the inside of the object, and thus the IR image is an image mainly showing luminescence from a target portion of the observation target. Considering such differences in property, the white light image is referred to as a surface image and the IR image is referred to as a luminescence image in the present embodiment.

The three-dimensional shape information estimation section 312 estimates the three-dimensional shape information of the target portion based on the surface image and the luminescence image. Details of the three-dimensional shape information will be described later.

The display image generation section 313 generates the display image based on the estimated three-dimensional shape information. Examples of the display image will be described later referring to FIGS. 16 and 17. The display image generation section 313 outputs the generated display image to the display section 400.

The external I/F section 500 is an interface used for input to the endoscope system by the user, for example. That is, the external I/F section 500 is an interface used to operate the endoscope system, to perform operation setting of the endoscope system, or the like. For example, the external I/F section 500 includes a button, a dial, a lever, or the like for operating the endoscope system.

Figure 3:
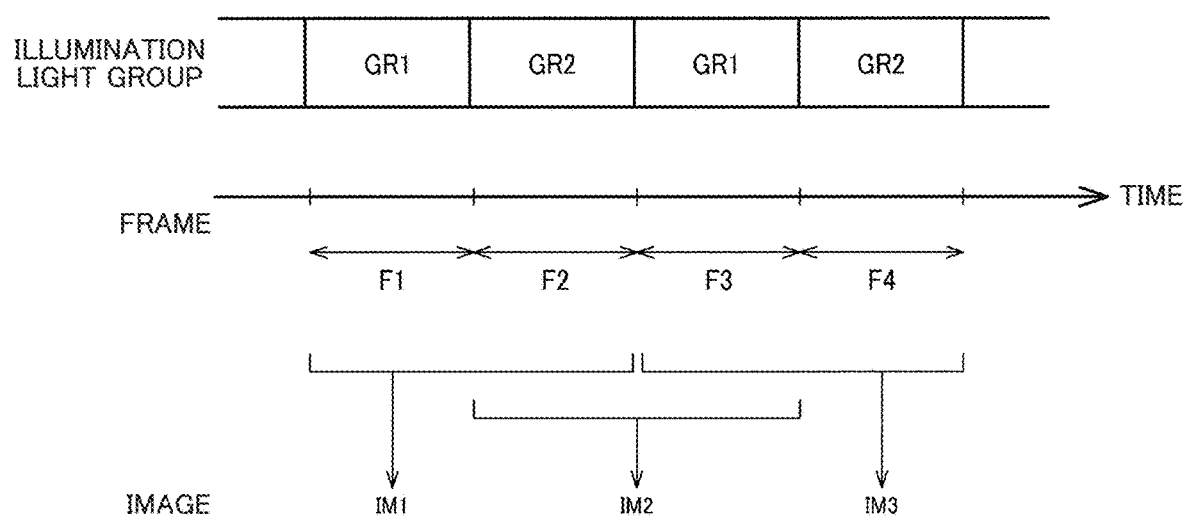
FIG. 3 is a diagram illustrating frame sequential imaging performed by the endoscope system according to the present embodiment.

FIG. 3 is a diagram illustrating frame sequential imaging performed by the endoscope system according to the present embodiment. As illustrated in FIG. 3, the light source device 100 emits a first illumination light group GR1 in a first frame F1, a second illumination light group GR2 in a second frame F2, the first illumination light group GR1 in a third frame F3, and the second illumination light group GR2 in a fourth frame F4. The frame is a period in which the image sensor 240 performs imaging, and corresponds to a frame in video filming. The emission timing of the illumination light can be set freely in one frame. Specifically, the light emission includes not only the continuous light emission, but also the pulse light emission, or limited light emission in a fixed period synchronized with a shutter timing of the image sensor.

The image sensor 240 captures images of the object illuminated by the first illumination light group GR1 in the first frame F1 and the third frame F3, and images of the object illuminated by the second illumination light group GR2 in the second frame F2 and the fourth frame F4.

The processing section 310 generates a first display image IM1 based on the images captured in the first frame F1 and the second frame F2. The processing section 310 also generates a second display image IM2 based on the images captured in the second frame F2 and the third frame F3, and a third display image IM3 based on the images captured in the third frame F3 and the fourth frame F4. The display images IM1 to IM3 become frame images in a video. This process is repeated thereafter to film the video, and the video is displayed on the display section 400.

Figure 4:
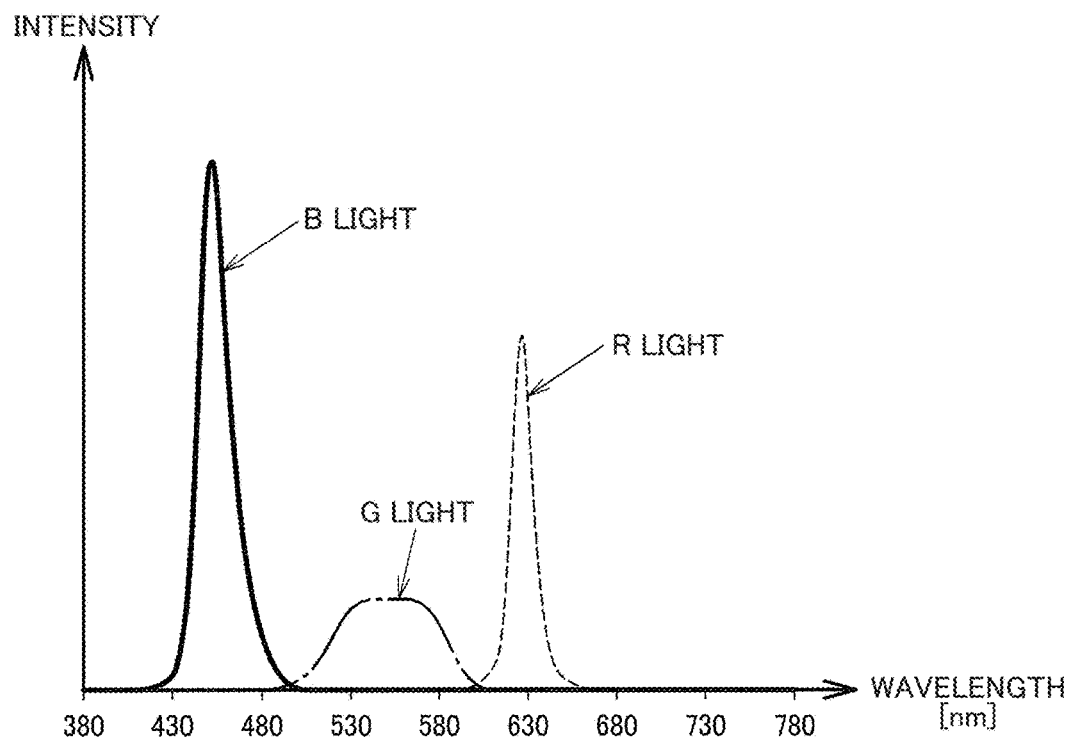
FIG. 4 is a graph illustrating a spectrum of illumination light.
Figure 5:
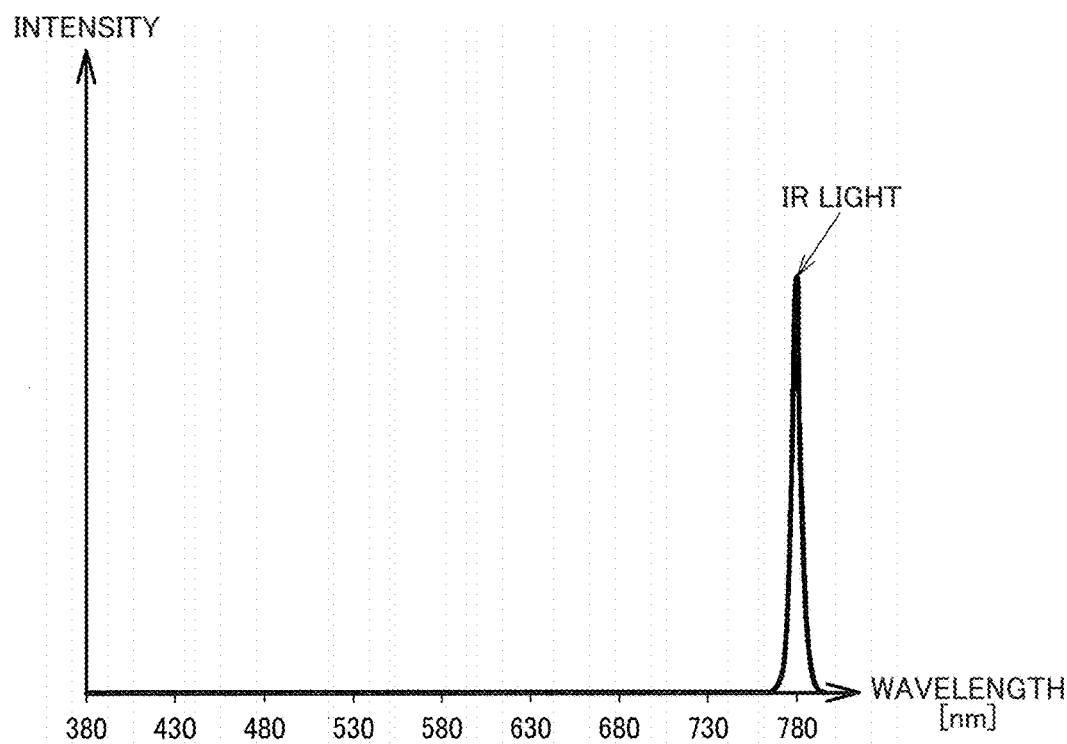
FIG. 5 is a graph illustrating a spectrum of illumination light.

FIGS. 4 and 5 are spectra of the illumination light. FIG. 4 illustrates a light spectrum included in the first illumination light group, and FIG. 5 illustrates a light spectrum included in the second illumination light group. The light source device 100 emits the B light, G light, and R light as the first illumination light group GR1 in FIG. 3, and the IR light as the second illumination light group GR2 in FIG. 3.

The image acquisition section 311 generates the R image, G image, and B image in the frames F1 and F3 in which the first illumination light group GR1 is emitted. More specifically, the image acquisition section 311 generates the white light image based on the R image, G image, and B image. The image acquisition section 311 generates the IR image in the frames F2 and F4 in which the second illumination light group GR2 is emitted. The image sensor 240 includes a pixel sensitive to the infrared light. For example, the image sensor 240 includes the R pixel, G pixel, and B pixel, and the R filter corresponding to the R pixel transmits the infrared light. In this case, the IR image is generated based on the output from the R pixel of the image sensor 240. Alternatively, the G filter and the B filter, corresponding to the G pixel and the B pixel, that transmit the infrared light may be used. In this case, the IR image is generated based on the output from the R pixel, G pixel, and B pixel of the image sensor 240. When the image sensor 240 includes the pixels sensitive to the infrared light in this manner, simultaneous emission of the R light, G light, B light, and IR light causes mixture of colors. However, emitting the first illumination light group GR1 and the second illumination light group GR2 at different timings as illustrated in FIG. 3 enables appropriate acquisition of the white light image and the IR image.

According to the present embodiment, however, the acquisition of the white light image and the IR image is only needed, and thus the configuration of the image sensor 240 and the light emission timing of the light source device 100 are not limited to the ones described above. For example, the image sensor 240 may include an IR pixel in addition to the R pixel, G pixel, and B pixel. An IR filter is disposed for the IR pixel. The IR filter hardly transmits a laser light of 780 nm, but transmits the light around 805 nm. In this case, the white light image and the IR image can be captured by simultaneously emitting the B light, G light, R light, and IR light. The endoscope system may also include a first image sensor for capturing the white light image and a second image sensor for capturing the IR image. In this case, the light transmitted by the objective lens 230 is divided into the visible light and the infrared light by a prism, a half mirror, or the like. The first image sensor receives the visible light and the second image sensor receives the infrared light. In this case also, the white light image and the IR image can be captured by simultaneously emitting the B light, G light, R light, and IR light.

Figure 6:
FIG. 6 is an example of a surface image.
Figure 7:
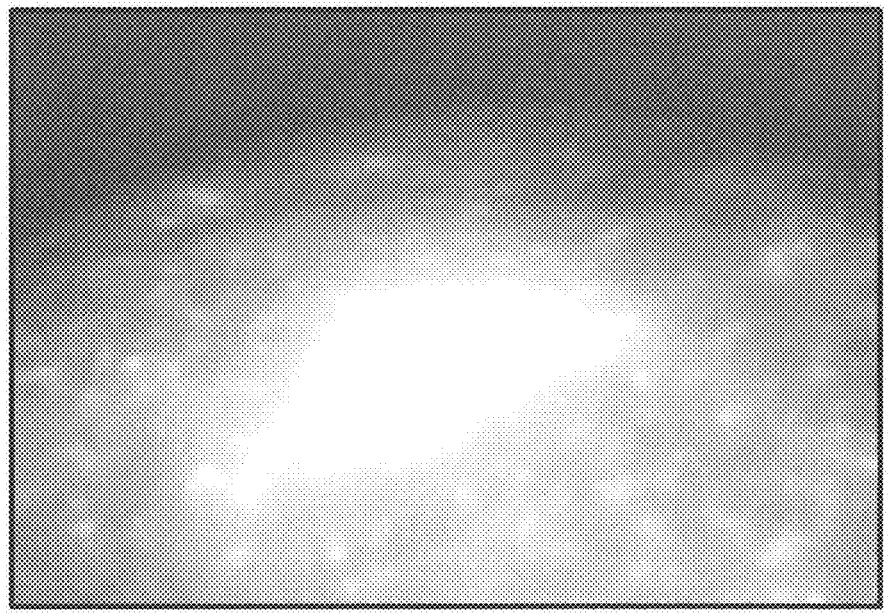
FIG. 7 is an example of a luminescence image.

FIG. 6 is an example of the white light image. FIG. 7 is an example of the IR image. The white light image is the surface image showing a surface structure of the observation target. The IR image is the luminescence image showing the target portion existing inside the observation target. A region having a high luminance value in the IR image is a region having strong fluorescence, that is, a region having a high accumulation degree of the ICG. FIG. 7 shows the region having the high luminance value in white. An example described herein is a case where the observation target is a liver, and the target portion is a tumor in the liver. However, the target portion only needs to be a structure inside the observation target, and is not limited to the tumor. The observation target is also not limited to the liver, and may be any other object such as a digestive tract.

Figure 8:
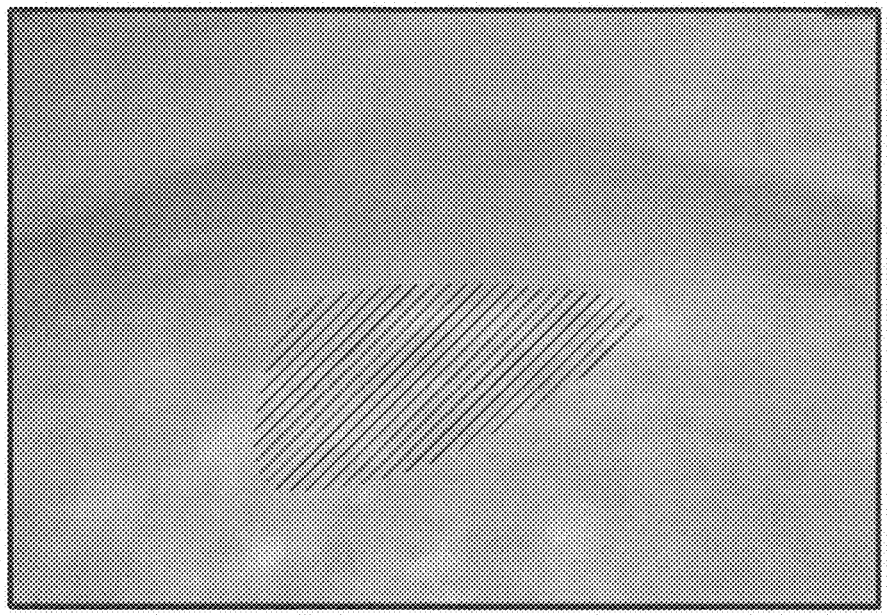
FIG. 8 is an example of a superimposed image.

There are conventionally known methods for generating a superimposed image by superimposing information about the target portion included in the IR image on the white light image. FIG. 8 is an example of a superimposed image, and a region applied with a superimposition process based on the IR image is shown by diagonal lines. In order to facilitate understanding of the drawing, only the region having an especially high luminance value in the IR image is used for the superimposition process. However, a generation process of the superimposed image can be modified in various manners. For example, the luminance value in the IR image may be converted into a different color in a color image so as to be superimposed on the white light image. For example, when a highlighting process is applied for making green stronger as the luminance value in the IR image becomes higher, a shade of green becomes strong in a region relating to the target portion such as the tumor. This can allow the user to recognize information on the target portion in the superimposed image.

The user, who is a surgeon or a physician, estimates a position and a size of the target portion in the observation target in the superimposed image, and performs treatment to the target portion. For example, the surgeon or physician performs the treatment to excise the target portion with a treatment tool. The treatment tool used here is an electric scalpel, a forceps, or the like. However, as understood from FIG. 8, the superimposed image is a two-dimensional image. Thus, a depth from the surface of the observation target to the target portion is not clear. Conventionally, the surgeon or physician estimates the depth of the target portion based on an expanse or a blurring degree of the region having the high luminance or the region in strong green in the IR image or the superimposed image so as to set an excision line. Accordingly, accuracy of the estimation of the depth depends on a degree of skill of the surgeon or physician, which makes it difficult to achieve the estimation with high accuracy. If the estimation of the depth can not be performed with high accuracy, the excision line needs to be set wider to prevent incomplete excision of the tumor or the like. Thus, a normal portion may be largely included in an excision target. On the other hand, if preservation of the normal portion is prioritized, a probability of the incomplete excision rises.

Meanwhile, there are known methods for acquiring a three-dimensional model of the observation target including the target portion by CT (computed tomography) or MRI (magnetic resonance imaging). With the three-dimensional model, the surgeon or physician can easily recognize the depth and shape of the target portion three-dimensionally. However, inspection using the CT or MRI needs to be performed with a dedicated device. This makes it difficult to acquire the three-dimensional model by the CT or MRI in real time during the treatment using the endoscope system. The surgeon or physician himself/herself needs to associate information based on the images acquired by the endoscope system, as shown in FIGS. 6 to 8, with information acquired by the CT or the like. Accordingly, experience and skill of the surgeon or physician are important to perform the treatment, such as the excision, appropriately.

Therefore, according to the present embodiment, the three-dimensional shape information that is the three-dimensional information of the target portion is estimated based on the surface image and luminescence image captured by the endoscope system.

The endoscope system according to the present embodiment includes the light source device 100, the image sensor 240, and the processing section 310. The light source device 100 emits the illumination light. The image sensor 240 captures the surface image of the surface shape of the observation target and the luminescence image of the luminescence from the target portion existing inside the observation target based on the illumination light. The processing section 310 estimates three-dimensional depth and shape information indicating the depth of the target portion of the observation target based on the surface image and the luminescence image. The estimated three-dimensional shape information is displayed on the display section 400, for example.

The surface shape used here is not limited to the shape of the surface itself that is a boundary surface between the observation target and an external space, but includes a shape of a region adjacent to the surface in the observation target. For example, the surface shape according to the present embodiment includes a shape of a region whose depth from the surface is equal to or shallower than a given depth threshold value.

The depth information used here is, specifically, numerical value data indicating a distance from the surface of the observation target to the target portion. However, the depth information only needs to be information capable of specifying the depth, and is not limited to the numerical value data indicating the distance. The three-dimensional shape information may include shape information of the target portion. The shape information used here is two-dimensional information on a shape of the target portion observed from a given viewpoint, for example. Alternatively, the shape information may be a set of two-dimensional information. For example, the shape information may be information including a shape of the target portion observed from a given viewpoint and a shape of the target portion observed from another viewpoint. The three-dimensional shape information according to the present embodiment only needs to be the three-dimensional information of the target portion, and may be the depth information only, or a combination of the depth information and the shape information.

According to the present embodiment, the three-dimensional information of the target portion can be estimated based on the two-dimensional surface image and luminescence image. With the three-dimensional shape information, an amount of information of the target portion increases compared with an amount of information in a conventional superimposed image illustrated in FIG. 8. This can suitably assist the user to make a diagnosis or perform treatment. Furthermore, the three-dimensional shape information according to the present embodiment is acquired based on the images captured by the endoscope system, unlike the information obtained by the CT or MRI. Accordingly, the three-dimensional shape information can be updated during the observation or treatment using the endoscope system. Furthermore, according to a method of the present embodiment, the information based on the two-dimensional images such as the surface image and the luminescence image can be easily associated with the three-dimensional shape information.

The illumination light emitted by the light source device 100 includes first illumination light for capturing the surface image, and second illumination light for capturing the luminescence image. The first illumination light and the second illumination light used here are light having different wavelengths, and not belonging to the same color in a narrow sense. For example, the first illumination light is the visible light, and the second illumination light is the infrared light. Alternatively, assuming that the wavelength band of the visible light is divided into the blue wavelength band, green wavelength band, and red wavelength band, when the first illumination light is in the blue wavelength band, the second illumination light is in the green or red wavelength band.

For example, the light source device 100 emits the white light and the infrared light as the illumination light to the observation target including the ICG pigment injected into the body, as illustrated in FIGS. 4 and 5. Specifically, the white light includes the B light, G light, and R light, and the infrared light includes the IR light. The light source that emits the white light is not limited to a combination of the light sources LDB, LDG, and LDR, and may be a combination of an LED of a predetermined color and a fluorescent body, or a light source other than the LED. The image sensor 240 captures the surface image based on the white light, and the luminescence image based on the infrared light. That is, the surface image is the white light image, and the luminescence image is the IR image corresponding to the fluorescence of the ICG.

As a result, when the target is a portion that tends to accumulate the ICG, suitable information can be provided to the user. An example described here is a case where the target portion is a tumor or a blood vessel in the liver. However, the treatment using the ICG can be widely applied to the treatment for various organs such as a kidney, a bladder, or a prostate. The illumination light is not limited to the white light and the infrared light, and can be modified in various manners. For example, the ICG is also known to emit the fluorescence when the red light in a visible light region is applied, and thus the infrared light can be replaced with the red light in the visible light region.

Furthermore, the method according to the present embodiment can be applied to a processing system including an acquisition section and a processing section. The processing system used here corresponds to the control device 300 in FIG. 1, for example. However, the processing system is not limited to this, and may be implemented by a server system that is connected to the endoscope system via a network, or by cloud computing. Alternatively, the processing system may be implemented by distributed processing between the control device 300 and a device such as a server system or the like.

The acquisition section acquires the surface image of the surface shape of the observation target and the luminescence image of the target portion existing inside the observation target. The acquisition section is an image transfer interface, a communication interface, or the like that acquires the images captured by the image sensor 240. The processing section estimates the three-dimensional shape information including at least one of the depth information indicating the depth from the surface of the observation target to the target portion and the shape information indicating the shape of the target portion based on the surface image and the luminescence image. The processing section used here may be the processing section 310 in FIG. 1 or a processor such as a server system.

As a result, the three-dimensional shape information based on the surface image and the luminescence image can be estimated by devices in various modes. For example, with the cloud computing, the estimation process is performed faster and more accurately, so that more suitable information can be presented to the user.

Furthermore, the method according to the present embodiment can be applied to an operation method of the endoscope system. The operation method of the endoscope system includes emitting the illumination light, capturing the surface image of the surface shape of the observation target and the luminescence image of the luminescence from the target portion existing inside the observation target based on the illumination light, and estimating the three-dimensional shape information including the depth information indicating the depth of the target portion of the observation target based on the surface image and the luminescence image.

Meanwhile, the control device 300 according to the present embodiment may be configured as follows. That is, each of the processing section 310 and the control circuit 320 is configured by hardware described below. Alternatively, the processing section (processing circuit) 310 and the control circuit 320 may be integrally configured by the hardware described below. The hardware may include at least one of a circuit that processes a digital signal and a circuit that processes an analog signal. For example, the hardware may include one or more circuit devices or one or more circuit elements mounted on a circuit board. The one or more circuit devices include an IC, for example. The one or more circuit elements include a resistor or a capacitor, for example.

Alternatively, each of the processing section 310 and the control circuit 320 may be implemented by a processor described below. Alternatively, the processing section 310 and the control circuit 320 may be implemented by a single processor. That is, the control device 300 according to the present embodiment includes a memory that stores information and a processor that operates based on the information stored in the memory. The memory used here is the storage section 330, for example. The information includes, for example, a program and various data. The processor includes hardware. The processor controls the light source device 100 to emit the illumination light. The processor controls the image sensor 240 to capture the surface image of the surface shape of the observation target and the luminescence image of the target portion existing inside the observation target. The processor estimates the three-dimensional shape information including the depth information indicating the depth from the surface of the observation target to the target portion and the shape information indicating the shape of the target portion based on the surface image and the luminescence image. Then, the processor controls the display section 400 to display the estimated three-dimensional shape information.

The processor may be a CPU (central processing unit), for example. However, the processor is not limited to the CPU, and may be any of various other processors such as a GPU (graphics processing unit) or a DSP (digital signal processor). The memory may be a semiconductor memory such as an SRAM or a DRAM, or may be a register. The memory may be a magnetic storage device such as a hard disk drive, or may be an optical storage device such as an optical disc device. For example, the memory may store a computer-readable instruction. A function of each of the sections of the control device 300 is implemented as a process when the processor executes the instruction. The instruction used here may be an instruction set included in a program, or may be an instruction that instructs a hardware circuit included in the processor to operate. For example, the processor implements the function of the processing section 310 in FIG. 1. Alternatively, the processor implements the functions of the processing section 310 and the control circuit 320 in FIG. 1.

Each of the sections of the endoscope system according to the present embodiment may be implemented as a module of a program that operates on the processor. For example, the program includes an image acquisition module for acquiring the surface image of the surface shape of the observation target and the luminescence image of the luminescence from the target portion existing inside the observation target, and a processing module for estimating the three-dimensional shape information including the depth information indicating the depth of the target portion of the observation target based on the surface image and the luminescence image.

Furthermore, the program that implements the processes performed by the sections of the control device 300 according to the present embodiment can be stored, for example, in a computer-readable device such as an information storage device. The information storage device can be implemented by an optical disk, a memory card, an HDD, or a semiconductor memory such as a nonvolatile memory or a RAM, for example. The processing section 310 and the control circuit 320 perform various processes according to the present embodiment based on the program and data stored in the information storage device. That is, the information storage device stores the program causing a computer to function as the sections of the endoscope system according to the present embodiment. The computer is a device including an input device, a processing section, a storage section, and an output section. The program causes the computer to execute the processes of these sections.

2. Estimation Process of Three-dimensional Shape Information Based on Surface Image and Luminescence Image Next, a process for estimating the three-dimensional shape information is described. A method using a geometric calculation and a method using machine learning are respectively described below.

2.1 Depth Information Estimation Based on Parameter

A depth that emission light can reach in the living body part depends on the wavelength of the emission light. For example, the IR light has a relatively long wavelength, and a relatively low degree of absorption by hemoglobin. Therefore, the IR light can reach deeper in the living body part than the visible light. When the target portion such as the tumor exists within a reachable depth, the ICG gathered and accumulated in the target portion emits fluorescence. The processing section 310 detects a region having the luminance value equal to or higher than a predetermined threshold value in the IR image as the target portion.

At this time, a property of the IR image differs depending on the depth of the target portion. For example, when the target portion is at a deep position, the blurring degree in a circumferential edge region of the target portion is high. The high blurring degree means that a size of a region having a luminance lower than a luminance of a central region of the target portion is large. In other words, the blurring degree is determined high when a gradient in the luminance value is low at a boundary portion between the target portion and a region other than the target portion.

As for the luminance of the entire target portion, the luminance is lower when the target portion is at a deep position compared with the luminance when the target portion is at a shallow position. The luminance of the entire target portion is information on a general tendency of the luminance at the target portion, and may be an average value or a highest value of the luminance in the entire target portion, for example. Alternatively, an average value of the luminance at part of the target portion may be used as the luminance of the entire target portion. The part of the target portion is the central region, for example. The luminance of the entire target portion is hereinafter referred to as an entire luminance.

As described above, the blurring degree and the entire luminance of the target portion can be used as parameters relating to the depth of the target portion. Since the depth where the target portion may exist depends on the wavelength of the illumination light as described above, the wavelength can also be used as a parameter relating to the depth. The processing section 310 estimates the depth information as the three-dimensional shape information based on these parameters.

For example, the endoscope system stores table data where the wavelength of the illumination light at the time of imaging of a given tumor, the blurring degree in the luminescence image captured using this illumination light, and the entire luminance are associated with the depth of the given tumor. The depth of the tumor may be measured using a removed living body part, or a value input by a skilled surgeon or physician may be used.

The processing section 310 obtains the blurring degree and the entire luminance from the luminescence image.

Then, the processing section 310 checks the wavelength of the illumination light used for imaging the luminescence image, and the obtained blurring degree and entire luminance against the table data. For example, the processing section 310 retrieves data having a similar wavelength, blurring degree, and entire luminance from the table data. Then, the processing section 310 sets the depth associated with the data determined to be most similar as the depth of the target portion.

Alternatively, a function for calculating the depth information based on the parameters may be obtained beforehand. The function used here is a function that performs correction processing based on the blurring degree and the entire luminance on a criterion depth set based on the wavelength of the illumination light so as to output the depth information, for example. The processing section 310 inputs the wavelength of the illumination light, and the blurring degree and entire luminance obtained from the luminescence image into the function to obtain the depth information of the target portion.

Unfortunately, the process using the luminescence image enables the estimation of how many millimeters deep from the surface of the living body part the target portion exists, but not a position of the surface of the living body part that is a criterion of the depth. In this regard, with a combination of the luminescence image and the surface image, the surface of the living body part as the criterion of the depth can be appropriately estimated. That is, the depth information of the target portion of the observation target can be estimated based on the surface image and the luminescence image.

2.2 Geometric Calculation Based on Viewpoint Information

The image sensor 240 captures a first surface image and a first luminescence image as the surface image and the luminescence image from a first viewpoint, and a second surface image and a second luminescence image as the surface image and the luminescence image from a second viewpoint different from the first viewpoint. Then, the processing section 310 may estimate the three-dimensional shape information based on the first surface image, first luminescence image, second surface image, and second luminescence image.

Using the surface images and the luminescence images captured from a plurality of viewpoints in such a manner enables accurate estimation of the three-dimensional shape information of the target portion. For example, using a two-dimensional image captured only from a single viewpoint enables identification of a direction connecting the image sensor 240 and the object, but not a specific distance. On the other hand, with the plurality of viewpoints, a specific three-dimensional position of the object can be identified. For example, the endoscope system according to the present embodiment includes a multi-eye camera including a plurality of imaging optical systems and the image sensors 240. An example including two viewpoints is described herein for convenience of explanation. However, a person skilled in the art can easily understand that three or more viewpoints can be included.

Figure 9:
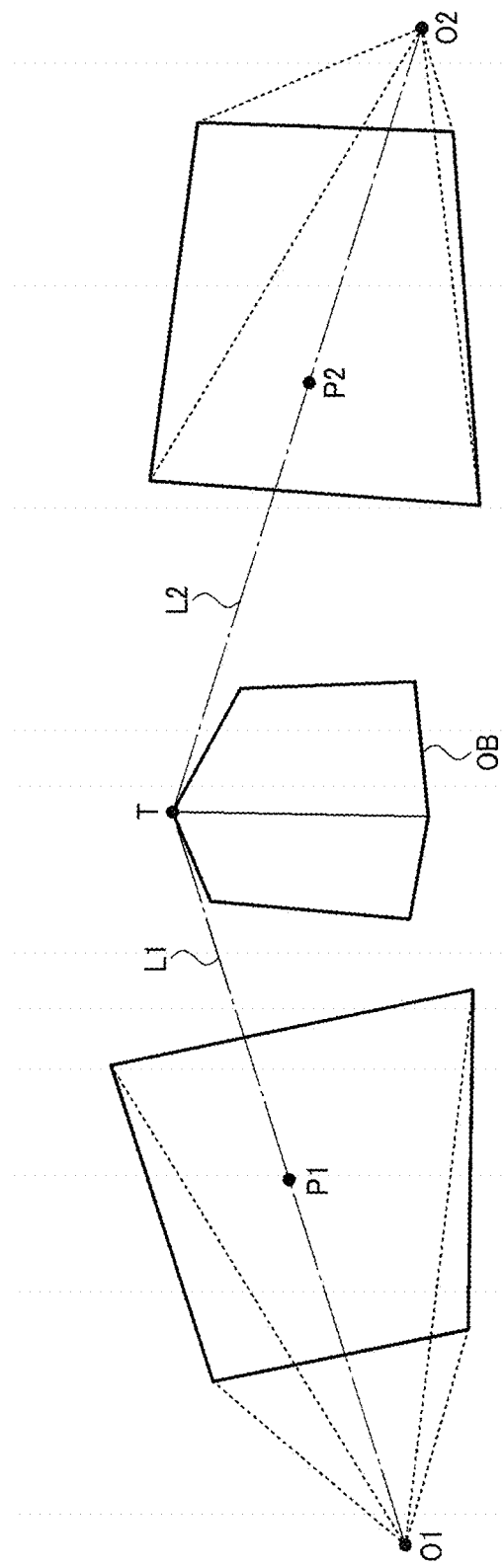
FIG. 9 is a schematic diagram of a process for obtaining three-dimensional shape information based on a geometric calculation.

FIG. 9 is a schematic diagram illustrating a method for estimating a three-dimensional position of an object in a plurality of two-dimensional images based on the plurality of two-dimensional images captured from different viewpoints. A quadrangular pyramid in FIG. 9 specifically has a rectangular base, and is a right pyramid whose perpendicular line from an apex O1 to the base corresponds to a gravity center of the rectangle. In FIG. 9, the apex O1 of the quadrangular pyramid represents the first viewpoint, and the perpendicular line from the apex O1 to the base represents an optical axis of the imaging optical system. A shape of the quadrangular pyramid is determined depending on an angle of view of the imaging optical system, and the base of the quadrangular pyramid corresponds to the captured image. When an object OB existing in a space is imaged from a viewpoint O1, a point T of the object OB is imaged at a position in the image corresponding to an intersection P1 of a line segment from the viewpoint O1 to the point T and the base of the quadrangular pyramid. Similarly, when the object OB is imaged from a viewpoint O2, the point T of the object OB is imaged at a position corresponding to an intersection P2 in the image.

As illustrated in FIG. 9, once the viewpoint O1 and the viewpoint O2, and a position P1 and a position P2 in the image corresponding to the point T on the object OB are identified, the three-dimensional position of the point T can be identified. Specifically, coordinates of the point T correspond to an intersection of a line L1 passing through the viewpoint O1 and the position P1 and a line L2 passing through the viewpoint O2 and the position P2.

As a result of the process described above, the three-dimensional position of a single point on the object is obtained. The process is repeated for other points on the object to obtain the three-dimensional positions of a plurality of points on the object.

Figure 10:
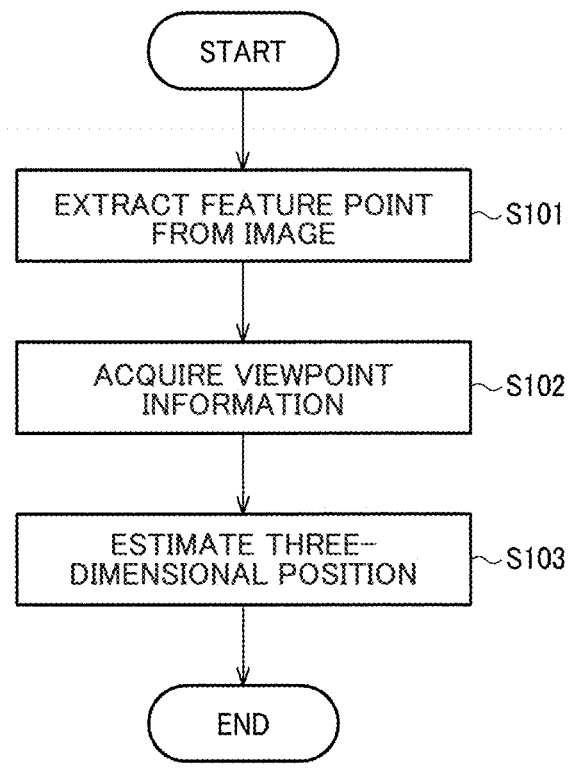
FIG. 10 is a flowchart illustrating an estimation process of the three-dimensional shape information.

FIG. 10 is a flowchart illustrating a process performed by the three-dimensional shape information estimation section 312. Firstly, the three-dimensional shape information estimation section 312 extracts a feature point from an image at a step S101. Specifically, the three-dimensional shape information estimation section 312 extracts corresponding feature points from the first surface image and the second surface image. For example, the extraction of the feature point is performed using SIFT (scale-invariant feature transform). For example, the three-dimensional shape information estimation section 312 respectively extracts the feature point from the first surface image and the feature point from the second surface image, and matches the feature points at the step S101. This allows identification of where a given position on the surface of the observation target is imaged in the first surface image and the second surface image. Similarly, the three-dimensional shape information estimation section 312 extracts the corresponding feature points from the first luminescence image and the second luminescence image.

Next, the three-dimensional shape information estimation section 312 acquires viewpoint information at a step S102. The viewpoint information used here is information identifying the first viewpoint and the second viewpoint, and specifically information identifying a position and a posture of a distal end of the insertion section 200. The position of the distal end of the insertion section 200 is represented by coordinate values (x, y, z) in respective axes in an XYZ space defined by an X axis, a Y axis, and a Z axis, for example. The posture of the distal end of the insertion section 200 is represented by angles (u, v, w) showing how much a current posture rotates around respective axes X, Y, and Z relative to a given criterion posture.

The process at the step S102 is performed using magnetic information, for example. For example, a magnetic coil unit is disposed at the distal end of the insertion section 200, and an external antenna detects the magnetic coil unit to obtain the position and posture of the distal end of the insertion section 200. For example, the three-dimensional shape information estimation section 312 acquires a signal from the external antenna in a period between the frame F1 and the frame F2 in FIG. 3 to identify the viewpoint information, and associates the viewpoint information with the surface image captured in the frame F1 and the luminescence image captured in the frame F2. Similarly, the three-dimensional shape information estimation section 312 acquires a signal from the external antenna in a period between the frame F3 and the frame F4 to identify the viewpoint information, and associates the viewpoint information with the surface information captured in the frame F3 and the luminescence image captured in the frame F4. However, timing and frequency to identify the viewpoint information can be modified in various manners.

Alternatively, the viewpoint information may be obtained based on image information. As for the image used here, either of the surface image and the luminescence image may be used. However, considering the accuracy of the process, the white light image of a color image, that is, the surface image is preferable. As described referring to FIG. 9, there is a correlation among the viewpoints O1 and O2, and the positions P1 and P2. That is, once a point P1 where a given object is imaged in the first surface image and a point P2 where the same object is imaged in the second surface image are identified, a change from the viewpoint O1 to the viewpoint O2, that is, a change in the position and posture can be identified. Accordingly, the three-dimensional shape information estimation section 312 estimates a change amount of the second viewpoint with respect to the first viewpoint based on how the feature point in the first surface image extracted at the step S101 has moved in the second surface image. For example, the three-dimensional shape information estimation section 312 identifies the viewpoint information based on the two surface images acquired in the frame F1 and the frame F3 in FIG. 3, and associates the viewpoint information with the surface image captured in the frame F1 and the luminescence image captured in the frame F2. Similarly, the three-dimensional shape information estimation section 312 identifies the viewpoint information based on the two surface images acquired in the frame F3 and a frame F5 subsequent to the frame F4, and associates the viewpoint information with the surface image captured in the frame F3 and the luminescence image captured in the frame F4. In this case also, the timing and frequency to identify the viewpoint information can be modified in various manners.

According to the present embodiment, only the identification of the viewpoint information including the first viewpoint and the second viewpoint is needed, and thus the magnetic information, the image information, or any other information may be used for that purpose.

Now, the viewpoints O1 and O2, and the positions P1 and P2 in FIG. 9 are identified by the steps S101 and S102. Accordingly, the three-dimensional shape information estimation section 312 estimates the three-dimensional position of the object based on the viewpoint information and the associated feature points at a step S103. Specifically, the three-dimensional shape information estimation section 312 obtains the three-dimensional position of the object imaged in the surface images, that is, the three-dimensional position of the surface of the observation target based on the first surface image and the second surface image. Similarly, the three-dimensional shape information estimation section 312 obtains the three-dimensional position of the target portion inside the observation target based on the first luminescence image and the second luminescence image. With the three-dimensional positions of both the surface of the observation target and the target portion, the three-dimensional shape information estimation section 312 can generate the three-dimensional shape information that enables understanding of a positional relationship between the surface of the observation target and the target portion.

The three-dimensional shape information estimation section 312 obtains the coordinates of a representative point on the surface of the observation target and the coordinates of a representative point of the target portion based on the geometric calculation described above, and calculates the depth information based on the two sets of coordinates. For example, the three-dimensional shape information estimation section 312 obtains a Euclidean distance between the two sets of coordinates as the depth information. In this case, the three-dimensional shape information estimation section 312 may perform a calculation for obtaining the three-dimensional coordinates of a single point as the geometric calculation based on the surface images captured from the plurality of viewpoints. Similarly, the three-dimensional shape information estimation section 312 performs the calculation for obtaining the three-dimensional coordinates of a single point of the target portion as the geometric calculation based on the luminescence images captured from the plurality of viewpoints. Furthermore, the three-dimensional shape information estimation section 312 may obtain a plurality of sets of coordinates of a plurality of representative points of both the surface of the observation target and the target portion, and obtain an average value of distances between corresponding representative points to calculate the depth information.

As described above, the processing section 310 identifies the first viewpoint and the second viewpoint. The processing section 310 estimates the three-dimensional information (position) of the surface of the observation target based on the geometric calculation using the identified first viewpoint and second viewpoint, the first surface image, and the second surface image, and the three-dimensional information of the target portion based on the geometric calculation using the identified first viewpoint and second viewpoint, the first luminescence image, and the second luminescence image. Then, the processing section 310 obtains the three-dimensional shape information based on results of the estimation. Acquiring the images captured from the plurality of viewpoints, and obtaining the viewpoint information on the plurality of viewpoints enable appropriate calculation of the relationship between the surface of the observation target and the target portion.

2.3 Machine Learning

Furthermore, the machine learning may be used for the estimation process of the three-dimensional shape information based on the surface image and the luminescence image. With the machine learning, the estimation process of the three-dimensional shape information based on the two-dimensional images can be implemented with high accuracy. A learning process and an inference process using a trained model are described below. The machine learning described below uses a neural network. However, the method according to the present embodiment is not limited to this. For example, according to the present embodiment, the machine learning using another model such as an SVM (support vector machine) may be performed, or the machine learning using a method developed from various methods such as the neural network or the SVM may be performed.

2.3.1 Learning Process

Figure 11:
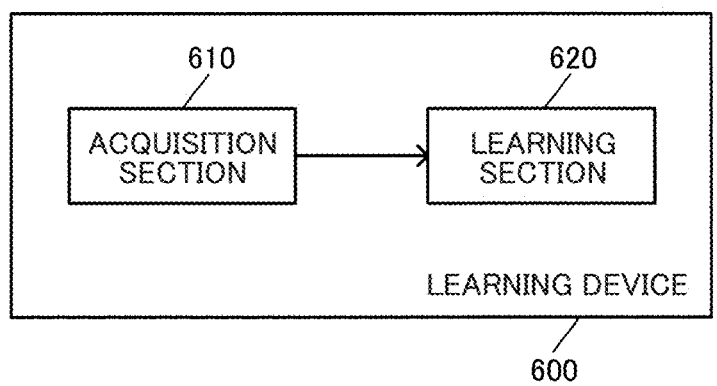
FIG. 11 is a configuration example of a learning device.

FIG. 11 is a diagram illustrating a configuration example of a learning device 600 according to the present embodiment. The learning device 600 includes an acquisition section 610 that acquires training data used for learning, and a learning section 620 that performs the machine learning based on the training data.

The acquisition section 610 is a communication interface that acquires the training data from another device, for example. Alternatively, the acquisition section 610 may acquire the training data stored in the learning device 600. For example, the learning device 600 includes a storage section unillustrated, and the acquisition section 610 is an interface that reads out the training data from the storage section. The learning according to the present embodiment is supervised learning, for example. The training data for the supervised learning include a dataset where input data and correct labels are associated. The learning section 620 performs the machine learning based on the training data acquired by the acquisition section 610 to generate a trained model.

The learning device 600 in FIG. 11 is included in a processing device different from the endoscope system, for example. The processing device may be a PC (personal computer), or a server system. The processing device sends the trained model generated by the learning process to the endoscope system. The learning device 600 may also be included in the endoscope system.

Figure 12:
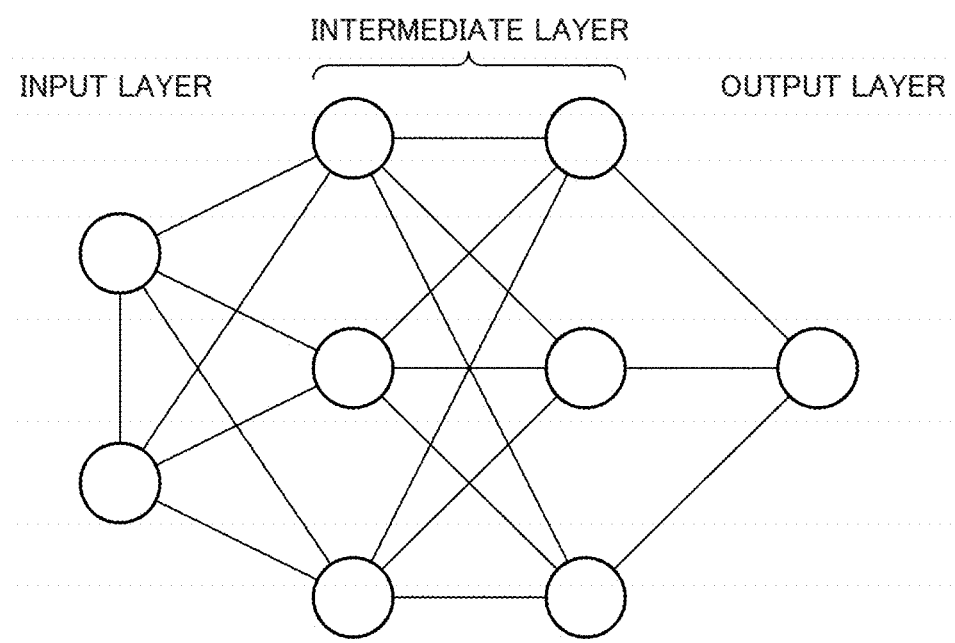
FIG. 12 is a configuration example of a neural network.

FIG. 12 is a schematic diagram illustrating the neural network. The neural network includes an input layer that accepts input data, an intermediate layer that performs a calculation based on output from the input layer, and an output layer that outputs data based on output from the intermediate layer. FIG. 12 illustrates an example of the network including two intermediate layers. However, a number of intermediate layers may be one, or three or more. In addition, a number of nodes (neurons) included in each layer is not limited to a number in the example in FIG. 12, and can be implemented in various modified manners. In view of accuracy, it is preferable to perform deep-layered learning (deep learning) using the neural network including multiple layers in the present embodiment. The multiple layers used here means four layers or more in a narrow sense.

As illustrated in FIG. 12, the nodes included in a given layer connect with the nodes in an adjacent layer. Each connection is set with a weight. For example, when a fully-connected neural network where each node in a given layer connects with all nodes in the next layer is used, a group of weights between these two layers includes a number of weights that is equal to a product of multiplication of a number of nodes included in the given layer and a number of nodes included in the next layer. Each node multiplies the output from previous nodes by the weights respectively and obtains a total value of multiplication results. In addition, the node further adds a bias to the total value, and applies an activation function to an addition result to obtain output of the node. The activation function includes a known ReLU function.

However, various functions are known to be adoptable as the activation function, and a sigmoid function, a function developed from the ReLU function, or any other function may be adopted.

The process described above is sequentially performed from the input layer to the output layer to obtain the output of the neural network. The learning by the neural network is a process of determining an appropriate weight (bias included). As for a specific learning method, various methods are known such as an error inverse propagation method, and any of these methods can be applied to the present embodiment. The error inverse propagation method is widely known, and thus detailed description is omitted.

However, the neural network is not limited to the configuration in FIG. 12. For example, the learning process and the inference process may use a CNN (convolutional neural network). The CNN includes a convolution layer that performs a convolution operation and a pooling layer, for example. The convolution layer is a layer that performs filter processing. The pooling layer is a layer that performs a pooling operation for reducing sizes in a vertical direction and a lateral direction. The weight of the convolution layer of the CNN is a parameter of a filter. That is, the learning by the CNN includes learning a filter property used for the convolution operation.

Figure 13:
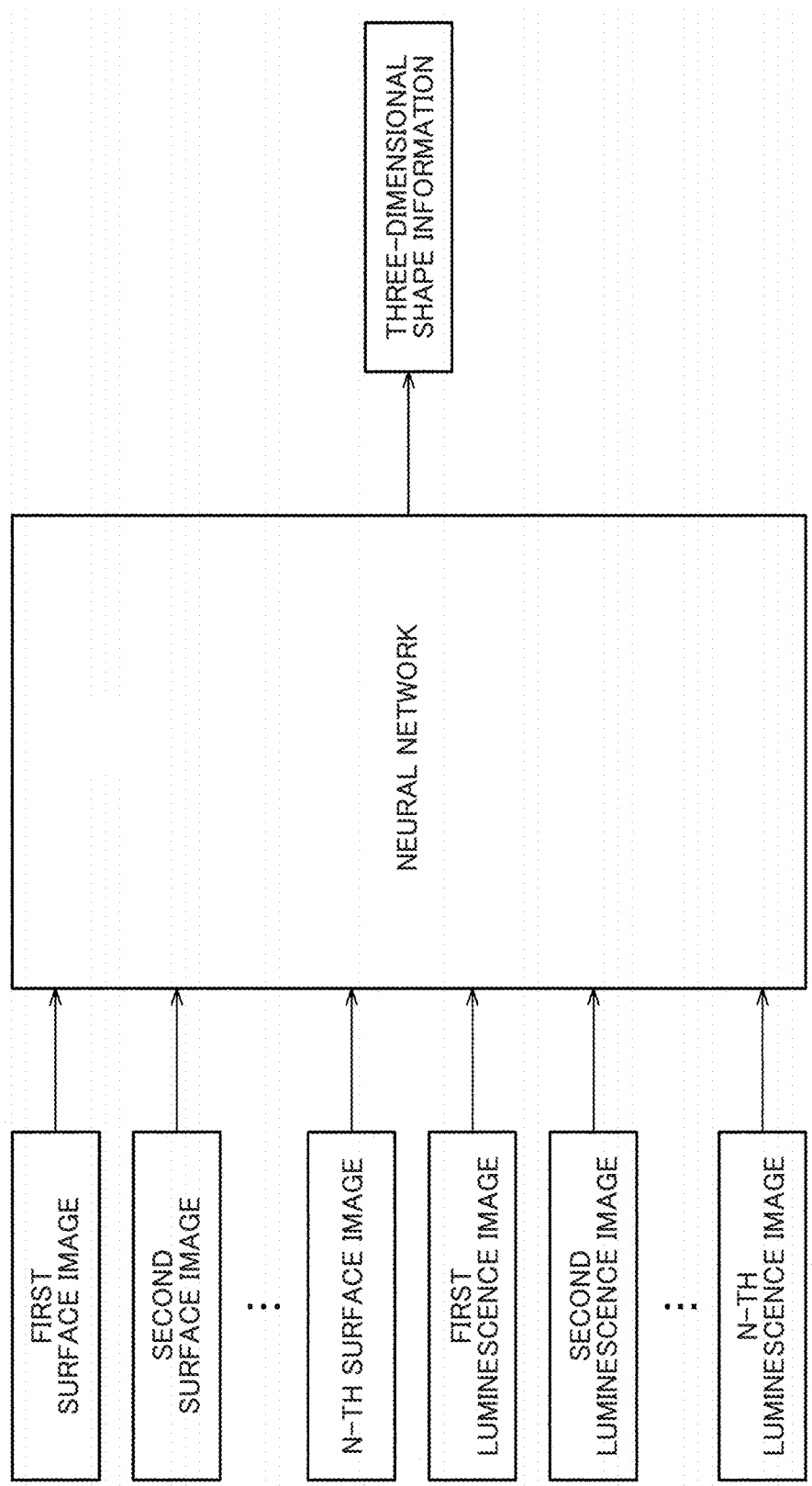
FIG. 13 is an example of input data and output data in machine learning.

FIG. 13 is a diagram illustrating the input and output in the machine learning according to the present embodiment. As illustrated in FIG. 13, the neural network according to the present embodiment accepts first to n-th surface images and first to n-th luminescence images as input. n used here is an integer of one or more. The neural network outputs the three-dimensional shape information. The training data according to the present embodiment are the dataset where correct three-dimensional shape information supposed to be generated from corresponding 2×n images is given to the first to n-th surface images and the first to n-th luminescence images as the correct labels. The three-dimensional shape information is the depth information of the target portion. For example, when the correct label is generated based on the removed living body part, the correct label can be generated by measuring the depth from the surface of the observation target to the target portion. Furthermore, the correct label may be the depth information estimated by a skilled surgeon or physician based on the surface image and the luminescence image. In this case, tacit knowledge possessed by the skilled surgeon or physician can be turned into AI (artificial intelligence).

In the learning process, the input data are firstly input in the neural network, and the calculation using the weights of that time is performed in a forward direction to acquire the output data. In the present embodiment, the input data are n surface images and n luminescence images. The output data obtained by the calculation in the forward direction is the depth information described above, for example.

The learning section 620 calculates an error function (loss function) based on the obtained output data and the correct label. For example, the error function is a function based on a difference between the depth information of the output data and the depth information given as the correct label. The learning section 620 updates the weights in a direction for reducing the error obtained by the error function. The error function is known in various forms, and any of them can be used in the present embodiment. Updating the weights is performed in the error inverse propagation method, for example. However, any other method may be used.

This is an outline of the learning process based on one set of data including the first to n-th surface images and the first to n-th luminescence images, and the depth information of the correct label. In the learning process, many sets of data are prepared, and the process described above is repeated to learn the appropriate weights. For example, in a learning stage, an endoscope system having a configuration similar to the configuration of the endoscope system according to the present embodiment is used to perform imaging and treatment so as to capture first to m-th surface images and first to m-th luminescence images. A relation here is m>n. In this case, the learning section 620 generates a plurality of sets of images by dividing the m surface images and m luminescence images respectively into n images. Then, the depth information as the correct label is given to each set of images to generate many sets of data.

Figure 14:
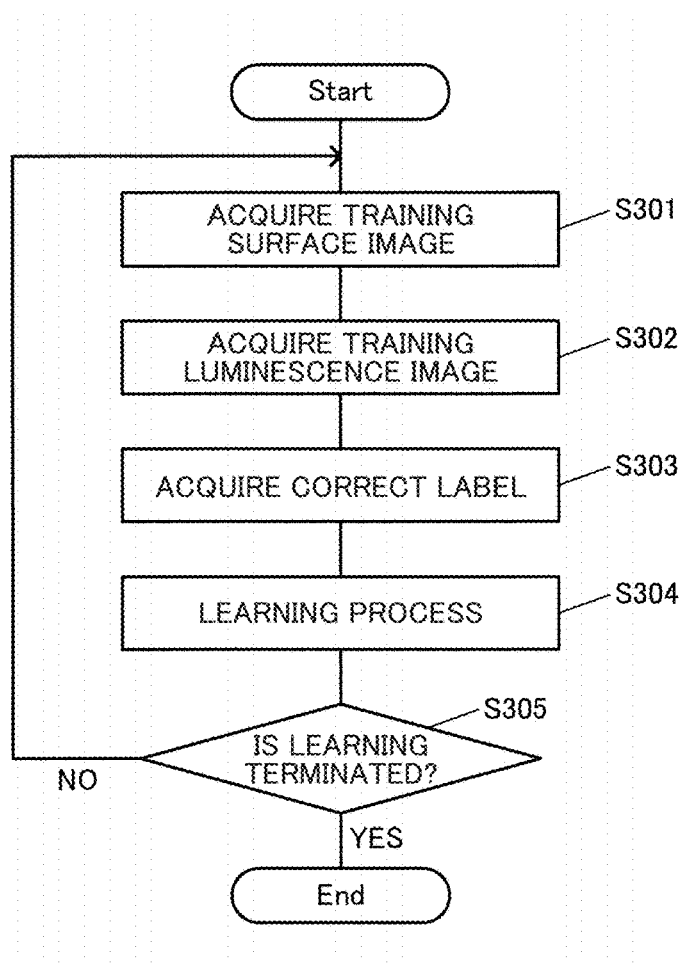
FIG. 14 is a flowchart illustrating a learning process.

FIG. 14 is a flowchart illustrating the process performed by the learning device 600. After the process is started, the acquisition section 610 of the learning device 600 acquires a training surface image of the white light image and a training luminescence image of the IR image at steps S301 and S302. The acquisition section 610 also acquires the depth information corresponding to the training surface image and the training luminescence image as the correct label at a step S303.

Then, the learning section 620 performs the learning process based on the acquired training data at a step S304. The process at the step S304 includes performing, based on one set of data, the calculation in the forward direction, the calculation of the error function, and the update of the weights based on the error function, for one time each, for example. Next, the learning section 620 determines whether to terminate the machine learning at a step S305. For example, the learning section 620 has divided the acquired many sets of data into training data and validation data in advance. Then, the learning section 620 performs a process using the validation data on the trained model obtained by the learning process based on the training data so as to determine the accuracy. Since the validation data include the associated depth information of the correct label, the learning section 620 can determine whether the depth information estimated based on the trained model is correct. Being correct used here means that the estimated depth information is sufficiently close to the depth information of the correct label. The learning section 620 determines to terminate the learning (Yes at the step S305) when a correct rate with respect to the validation data is equal to or higher than a predetermined threshold value, and terminates the process. Alternatively, the learning section 620 may determine to terminate the learning after performing the process at the step S304 for a predetermined number of times. The trained model generated by the learning process is stored in the storage section 330 in the endoscope system.

2.3.2 Inference Process

The endoscope system according to the present embodiment performs the inference process using the trained model. Specifically, the processing section 310 of the endoscope system reads out the trained model from the storage section 330, and performs the calculation in accordance with the trained model to estimate the three-dimensional shape information.

The trained model is used as a program module that is part of artificial intelligence software. The processing section 310 outputs the data indicating the three-dimensional shape information corresponding to the input surface image and luminescence image in accordance with an instruction from the trained model stored in the storage section 330.

The calculation by the processing section 310 in accordance with the trained model, that is, the calculation for outputting the output data based on the input data may be performed by software or hardware. In other words, the convolution operation in the CNN or the like may be performed as software. Alternatively, the calculation described above may be performed by a circuit device such as an FPGA (field-programmable gate array). The calculation described above may also be performed by a combination of software and hardware. The operation of the processing section 310 in accordance with the instruction from the trained model stored in the storage section 330 can be implemented in various manners. For example, the trained model includes an inference algorithm and a parameter used for the inference algorithm. The inference algorithm is an algorithm that performs a product-sum operation, the convolution operation, or the like based on the input data. The parameter is a parameter obtained by the learning process, such as the weight in the neural network. In this case, both the inference algorithm and the parameter are stored in the storage section 330, and the processing section 310 may read out the inference algorithm and the parameter to perform the inference process as software. Alternatively, the inference algorithm may be implemented by the FPGA or the like, and the storage section 330 may store the parameter.

Figure 15:
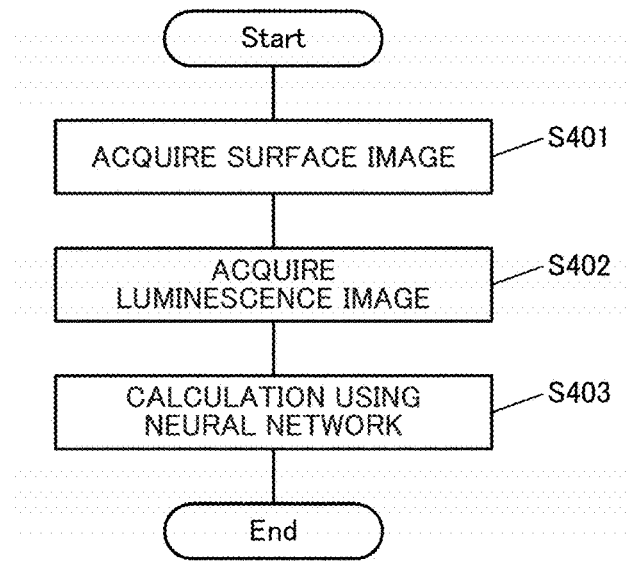
FIG. 15 is a flowchart illustrating an inference process.

FIG. 15 is a flowchart illustrating the inference process performed at the processing section 310. After the process is started, the image acquisition section 311 acquires the surface image of the white light image and the luminescence image of the IR image at steps S401 and S402. Then, the processing section 310 operates in accordance with the instruction from the trained model stored in the storage section 330 to estimate the three-dimensional shape information of the target portion at a step S403. Specifically, the processing section 310 performs the calculation using the neural network with n surface images and n luminescence images as the input data.

As described above, the endoscope system according to the present embodiment may include the storage section 330 that stores the trained model. The trained model is obtained by the machine learning based on the dataset where the correct labels corresponding to the three-dimensional shape information are given to the training surface image of the surface shape of the observation target, and the training luminescence image of the target portion. Then, the processing section 310 estimates the three-dimensional shape information based on the surface image and luminescence image captured by the image sensor 240 and the trained model.

As a result, the three-dimensional shape information based on the surface image and the luminescence image can be estimated based on the trained model. With the machine learning performed using a large number of training data, the process using the trained model can be performed with high accuracy.

Meanwhile, the trained model may be obtained by the machine learning based on a dataset where the correct labels are given to the plurality of training surface images captured from the plurality of different viewpoints, and the plurality of training luminescence images captured from the plurality of different viewpoints. In this case, the image sensor 240 of the endoscope system captures the first surface image and the first luminescence image as the surface image and the luminescence image from the first viewpoint, and the second surface image and the second luminescence image as the surface image and the luminescence image from the second viewpoint different from the first viewpoint. Then, the processing section 310 estimates the three-dimensional shape information based on the first surface image, first luminescence image, second surface image, and second luminescence image, and the trained model. That is, n described above may be an integer of two or more.

As described above referring to FIG. 9, when estimating the three-dimensional shape based on the two-dimensional image, using a plurality of images captured from different viewpoints is useful. Also, when using the machine learning, using the plurality of surface images and plurality of luminescence images captured from the different viewpoints as the input data can improve the accuracy of the estimation of the three-dimensional shape information.

However, in a field of machine learning, a method for estimating the three-dimensional shape from a single two-dimensional image is known. In other words, information in a depth direction that is lost in the two-dimensional image can be complemented by the machine learning. Accordingly, the input data for the machine learning according to the present embodiment may be one surface image and one luminescence image. That is, n described above may be one. In this manner, the three-dimensional shape information can be estimated from a fewer number of images. This method does not require accumulating a large number of images for estimating the three-dimensional shape information, and reduces a load of the estimation process. Thus, the three-dimensional shape information can be output quickly.

2.3.3 Modification of Machine Learning

As illustrated in FIG. 13, the input data for the machine learning includes one or more surface images and one or more luminescence images. However, the input data is not limited to this, and any additional data may be further included.

The trained model may be obtained by the machine learning based on a dataset where correct labels are given to the training surface image, the training luminescence image, and additional information. The processing section 310 acquires the surface image, the luminescence image, and the additional information, and estimates the three-dimensional shape information based on the acquired surface image, luminescence image, and additional information, and the trained model. In this manner, the machine learning using the additional information can improve the accuracy of the estimation of the three-dimensional shape information.

The additional information used here is illumination information of the light source device 100, for example. The illumination information includes spectrum information, light amount information, light emission timing information, light emission period information, and light distribution information. The spectrum information is information indicating the spectrum of the illumination light as illustrated in FIGS. 4 and 5. The light amount information is information specifying a light emission intensity of each illumination light. The light emission timing information is information specifying a light emission timing of each light source. The light emission period information is information specifying a period when each light source emits light or a period when each light source does not emit light. The light distribution information is information specifying a light emission intensity with respect to a direction of each light source, and is a light distribution curve, for example. With the illumination information, the machine learning considering specific configurations of the light source device 100 can be performed.

The additional information may also be imaging information relating to the image sensor 240. The imaging information includes sensitivity information, angle of view information, diaphragm value information, magnification information, resolution information, and number of pixels information. The sensitivity information is information indicating the sensitivity of the image sensor, and information associating the wavelength band with the sensitivity, for example. The angle of view information is information specifying the angle of view of the imaging optical system. The diaphragm value information is information specifying an F value of the imaging optical system. The magnification information is information specifying a lens included in the imaging optical system, specifically, the magnification of the objective lens 230. The resolution information is information specifying the resolution of the image sensor 240, and information indicating the number of pixels per predetermined length, for example. The number of pixels information is information specifying the number of pixels of the image sensor, and information on the number of pixels in a vertical direction and the number of pixels in a horizontal direction, for example. With the imaging information, the machine learning considering specific configurations of the imaging optical system including the image sensor 240 can be performed.

The additional information may also be observation target information relating to the observation target. The observation target information includes age information, gender information, medical history information, body temperature information, observation image information acquired in the past, and observation region information. The age information, gender information, medical history information, and body temperature information is information indicating the age, gender, medical history, and body temperature of a patient to be diagnosed and treated, respectively. The medical history information includes information specifying a disease that the patient had in the past, and information specifying a timing when the patient had the disease, for example. The observation target information may also include other monitoring data relating to the patient such as blood pressure or a blood test result of the patient. The observation image information acquired in the past is an image acquired in the treatment performed on the patient in the past, and includes the surface image and the luminescence image captured using the endoscope system, for example. The observation region information is information specifying a region to be the observation target, such as an organ. With the observation target information, the machine learning considering detailed information on the patient can be performed.

According to the example described above, the machine learning is used for the entire process of estimating the three-dimensional shape information based on the surface image and the luminescence image. However, the process applied with the machine learning is not limited to this. For example, as described above referring to FIG. 10, the process using the geometric calculation includes two steps including identifying the viewpoint and generating the three-dimensional shape information based on the identified viewpoint. According to the present embodiment, the machine learning may be used for one of these steps.

For example, the trained model is obtained by the machine learning based on a dataset where the viewpoint information is given as the correct labels to the input data including the surface image and the luminescence image. In this case, the three-dimensional shape information estimation section 312 acquires the surface image and the luminescence image, and estimates the viewpoint based on the acquired surface image and luminescence image and the trained model. This process is performed on at least two sets of the surface image and the luminescence image to acquire the first surface image, first luminescence image, second surface image, and second luminescence image, and the viewpoint information indicating the first viewpoint and the second viewpoint. The three-dimensional shape information estimation section 312 preforms the geometric calculation illustrated in FIG. 9 to estimate the three-dimensional shape information.

Alternatively, the three-dimensional shape information estimation section 312 may estimate the viewpoint information by the geometric calculation based on the first surface image, first luminescence image, second surface image, and second luminescence image. Then, the three-dimensional shape information estimation section 312 estimates the three-dimensional shape information based on the input data including the surface image, the luminescence image, and the viewpoint information, and the trained model. Inputting the viewpoint information enables the machine learning including directions from which the surface image and the luminescence image are captured. This can improve the accuracy of the estimation of the three-dimensional shape information. The viewpoint information may be obtained based on the magnetic information as described above.

The estimation of the three-dimensional shape information according to the present embodiment may be performed based on the geometric calculation, the machine learning, or the combination of the geometric calculation and the machine learning, as described above.

3. Display Process

As described above, the endoscope system according to the present embodiment includes the display section 400, and the processing section 310 performs a process for displaying the estimated three-dimensional shape information on the display section 400.

As described above, when the treatment such as excision is performed on the target portion, the depth from the surface of the observation target to the target portion is important. Accordingly, the processing section 310 may display the depth information on the display section 400.

Figure 16:
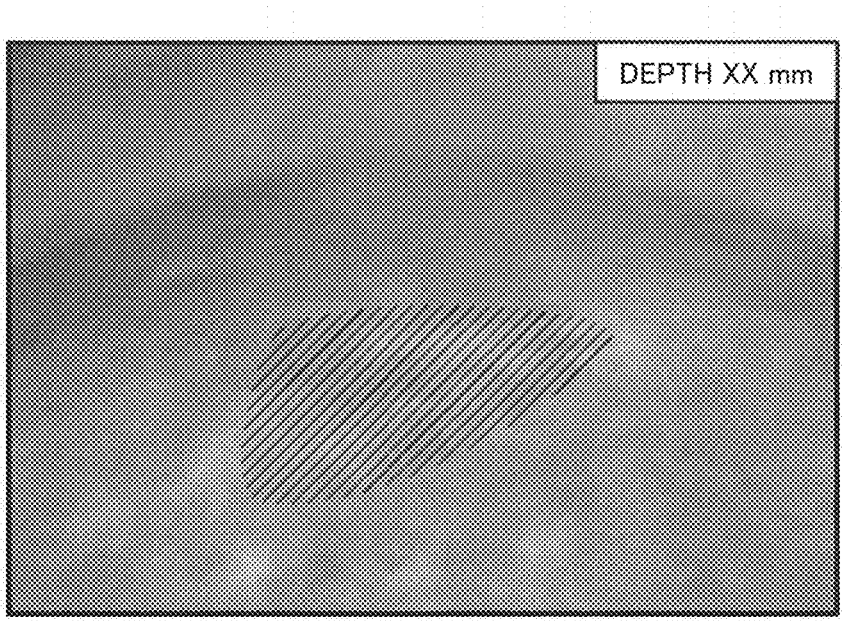
FIG. 16 is an example of a display screen displaying the three-dimensional shape information of depth information.

FIG. 16 is an example of a display screen displaying the depth information. The display section 400 displays an image where the depth represented by the depth information is added to a display image based on the surface image or the luminescence image. In the example in FIG. 16, the display image based on the surface image or the luminescence image is the superimposed image similar to the image in FIG. 8. However, the display image may be the surface image or the luminescence image. Furthermore, in the example in FIG. 16, text that reads "depth xx mm" (xx is a specific numerical value) is displayed at an upper right of a screen. However, a specific display design is not limited to this. Displaying the depth information in such a manner can appropriately assist the user to make a diagnosis or perform treatment.

The processing section 310 may also generate support information for supporting the user to perform the treatment on the target portion based on the three-dimensional shape information. The display section 400 displays the support information. This can appropriately assist the user to make a diagnosis or perform treatment.

Figure 17:
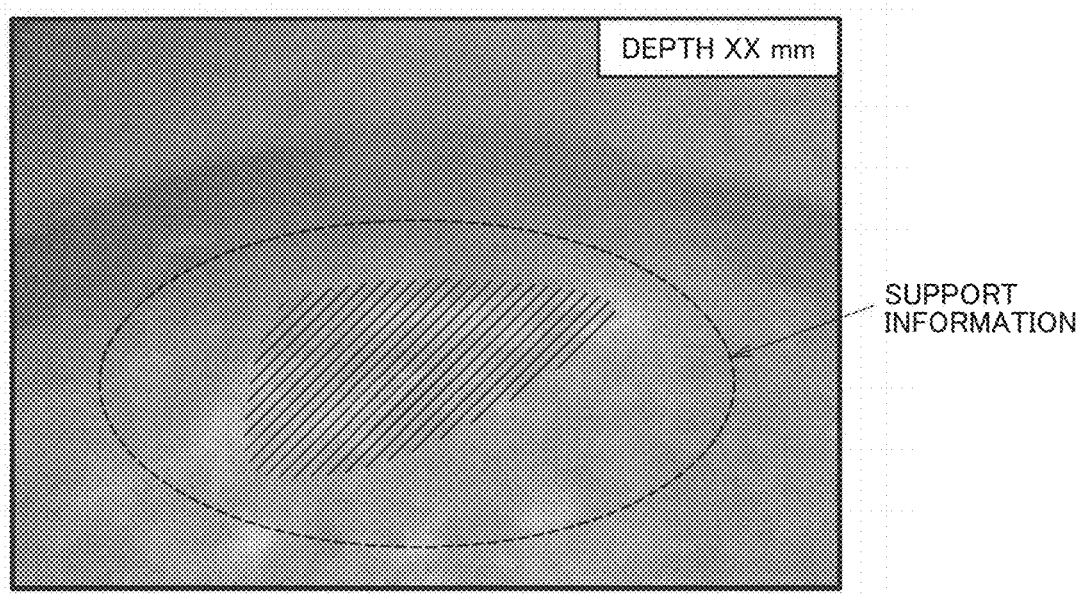
FIG. 17 is an example of a display screen displaying support information.

FIG. 17 is an example of the display screen displaying the support information. As illustrated in FIG. 17, the support information may be information indicating an excision position for excising the target portion. The display section 400 displays an image where the excision position is distinguishably displayed on the display image. FIG. 17 shows an example where the display image is the superimposed image and the excision position is shown by a broken line. Accordingly, the user can easily perform the treatment by performing the excision along the excision position indicated by the support information. As a result, incomplete excision of the tumor or the like, and excessive excision of the normal portion can be reduced.

Alternatively, the processing section 310 may perform a process for detecting a position of a treatment target to be treated by the user, and may generate alert information as the support information based on the position of the treatment. For example, the alert information is information alerting that the excision of the tumor or the like is incomplete. The alert information may be text information or image information indicating the alert. Furthermore, the alert may be given by sound output from a speaker or light emission by a light emitting section such as an LED along with the display of the alert information. The processing section 310 detects a position of a treatment tool such as an electric scalpel based on the surface image or the magnetic information so as to determine a position where the excision has been actually performed. Then, when the processing section 310 determines that the excision is incomplete based on a comparison process between the three-dimensional shape information of the target portion and the position where the excision has been performed, the processing section 310 generates and displays the alert information. This can appropriately assist the user to make a diagnosis or perform treatment. The alert information may be information alerting that the normal portion is being excessively excised, or any other information.

Although only the present embodiment is described in detail above, those skilled in the art will readily appreciate that many modifications are possible without materially departing from the novel teachings and advantages of the present embodiment. Accordingly, all such modifications are intended to be included within the scope of the present disclosure. For example, any term cited with a different term having a broader meaning or the same meaning at least once in the specification and the drawings can be replaced by the different term in any place in the specification and the drawings. All combinations of the present embodiment and modifications are also included in the scope of the present disclosure. The configurations and the operations of the endoscope system, a processing system, or the like are not limited to those described above in connection with the present embodiment. Various modifications and variations may be made of those described above in connection with the present embodiment.

What is claimed is:

1. A control device comprising
one or more processors comprising hardware, wherein the one or more processors are configured to:
acquire a first surface image of a surface of an observation target captured by an image sensor at a first viewpoint, and a first inside image of a target portion inside the observation target captured by the image sensor at the first viewpoint;
acquire a second surface image of the surface of the observation target captured by the image sensor at a second viewpoint, and a second inside image of the target portion at the second viewpoint;
calculate three-dimensional coordinates of the surface based on the first and second surface images;
calculate three-dimensional coordinates of the target portion based on the first and second inside images; and
estimate depth information indicating a depth from the surface to the target portion based on the three-dimensional coordinates of the surface and the three-dimensional coordinates of the target portion.

2. The control device according to claim 1,
wherein the one or more processors are configured to:
acquire first and second viewpoint information on the first and second viewpoints, respectively;
calculate the three-dimensional coordinates of the surface based on the first surface image, the second surface image, and the first viewpoint information; and
estimate the three-dimensional coordinates of the target portion based on the first inside image, the second inside image, and the second viewpoint information.

3. The control device according to claim 2,
wherein the one or more processors are configured to:
   calculate the first viewpoint information based on the first surface image and the first inside image; and
   calculate the second viewpoint information based on the second surface image and the second inside image.

4. The control device according to in claim 1, further comprising a storage device configured to store a trained model,
wherein the trained model is obtained by machine learning based on a dataset where correct labels corresponding to the depth information are given to a training surface image of the surface of the observation target and a training inside image of the target portion, and
wherein the one or more processors are configured to estimate the depth information based on the first surface image, the second surface image, the first inside image, the second inside image, and the trained model.

5. The control device according to claim 1, wherein the one or more processors are configured to:
   generate a display image including the depth information based on the first surface image, the second surface image, the first inside image and the second inside image; and
   output the display image.

6. The control device according to claim 1, wherein:
each of the first surface image and the second surface image is a two-dimensional image captured under white light; and
each of the first inside image and the second inside image is a two-dimensional image of luminescence of the target portion, captured under infrared light.

7. The control device according to claim 2,
wherein the first and second viewpoint information includes information on three-dimensional coordinates and a posture of a distal end of an insertion section including the image sensor that captured the first and second surface images and the first and second inside images,
the three-dimensional coordinates of the surface are calculated in real time, and
the three-dimensional coordinates of the target portion are calculated in real time.

8. An image processing method comprising:
acquiring a first surface image of a surface of an observation target captured by an image sensor at a first viewpoint, and a first inside image of a target portion inside the observation target captured by the image sensor at the first viewpoint;
acquiring a second surface image of the surface of the observation target captured by the image sensor at a second viewpoint, and a second inside image of the target portion at the second viewpoint;
calculating three-dimensional coordinates of the surface from the first and second surface images;
calculating three-dimensional coordinates of the target portion from the first and second inside images; and
estimating depth information indicating a depth from the surface to the target portion based on the three-dimensional coordinates of the surface and the three-dimensional coordinates of the target portion.

9. A non-transitory computer-readable storage medium configured to store a program that causes a computer to at least perform:
acquiring a first surface image of a surface of an observation target captured by an image sensor at a first viewpoint, and a first inside image of a target portion inside the observation target captured by the image sensor at the first viewpoint;
acquiring a second surface image of the surface of the observation target captured by the image sensor at a second viewpoint, and a second inside image of the target portion at the second viewpoint;
calculating three-dimensional coordinates of the surface based on the first and second surface images;
calculating three-dimensional coordinates of the target portion based on the first and second inside images; and
estimating depth information indicating a depth from the surface to the target portion based on the three-dimensional coordinates of the surface and the three-dimensional coordinates of the target portion.

10. The control device according to claim 1, wherein the one or more processors are configured to determine the target portion where luminance value equal to or higher than a predetermined luminance value in the first inside image or the second inside image.

11. The control device according to claim 10, wherein the one or more processors are configured to:
   determine a gradient in the luminance value at a boundary portion between the target portion and a region other than the target portion; and
   estimate the depth information based on the gradient in the luminance value.

12. The control device according to claim 11, further comprising a storage device configured to store a database, the database storing the depth information, the luminance value, and a blurring degree associated with each other,
wherein the one or more processors are configured to reference the database for the depth information estimated.

13. The control device according to claim 1, wherein the one or more processors are configured to:
   extract a first and second feature points from the first and second surface images, respectively; and
   match the first and second feature points.

14. The control device according to claim 13, wherein the one or more processors are configured to estimate a change amount of the second viewpoint with respect to the first viewpoint based on first and second feature points.

15. The control device according to claim 1, wherein the one or more processors are configured to:
   receive at least one of: (i) a first and second coordinate values; and (ii) a first and second angles, at the first and second viewpoints, respectively; and
   estimate the depth information based on at least one of: (i) the first and second coordinate values, and (ii) the first and second angles.

16. The control device according to claim 1, wherein:
the one or more processors are configured to acquire the first surface image, the first inside image, the second surface image and the second inside image in this order; and
the first surface image, the first inside image, the second surface image and the second inside image are acquired by a single image sensor.

17. The control device according to claim 5, wherein the display image further includes an excision position for excising the target portion.

18. The control device according to claim 1, wherein the one or more processors are configured to estimate the depth information including a three-dimensional shape of the target portion based on the first and second surface images and the first and second inside images.

19. The control device according to claim 1, wherein the one or more processors are configured to:
- convert a color of the target portion in the first and second inside images into a different color;
- generate a display image including the depth information based on the first and second surface images and the first and second inside images converted; and
- output the display image.

20. The control device according to claim 2, wherein the one or more processors are configured to:
- associate with the first viewpoint information and the first surface image and the first inside image; and
- associate with the second viewpoint information and the second surface image and the second inside image.

* * * * *